United States Patent [19]
Sakai

[11] Patent Number: 6,013,042
[45] Date of Patent: Jan. 11, 2000

[54] MASSAGING DEVICE FOR FEET AND LEGS

[75] Inventor: Sadami Sakai, Fukui, Japan

[73] Assignee: Todoroki Sangyo Kabushiki Kaisha, Fukui, Japan

[21] Appl. No.: 09/011,144

[22] PCT Filed: Jun. 10, 1997

[86] PCT No.: PCT/JP97/01977

§ 371 Date: Feb. 3, 1998

§ 102(e) Date: Feb. 3, 1998

[30] Foreign Application Priority Data

Feb. 18, 1997 [JP] Japan .................................. 9-34036

[51] Int. Cl.⁷ .................................................. A61H 7/00
[52] U.S. Cl. .............................. 601/134; 601/28; 5/648; 5/651
[58] Field of Search ............................. 601/134, 27, 28; 5/648, 651; 482/142, 146; 297/423, 44

[56] References Cited

U.S. PATENT DOCUMENTS

| | | | |
|---|---|---|---|
| 2,644,688 | 7/1953 | Roberge | 272/57 |
| 2,895,470 | 7/1959 | Reiter | 601/122 |
| 4,692,954 | 9/1987 | Scott, Sr. | 5/648 |
| 5,056,507 | 10/1991 | Yum | 601/136 |
| 5,382,222 | 1/1995 | Yih-Jong | 601/15 |

FOREIGN PATENT DOCUMENTS

| | | | |
|---|---|---|---|
| 1194545 | 12/1959 | France | 601/131 |
| 1544428 | 2/1990 | U.S.S.R. | 601/28 |

*Primary Examiner*—Richard J. Apley
*Assistant Examiner*—Benjam Koo
*Attorney, Agent, or Firm*—Snider & Associates; Ronald R. Snider

[57] ABSTRACT

The present invention aims to provide a massaging device for feet and legs comprising a number of bosses each having a spherically headed portion on the top and lined on platforms of a certain height in plural rows, characterized in that the users can casually use it concurrently with their work in the office and not only the vital points of those body portions can be comfortably and adequately stimulated from an optimum angle with respect to those vital points just by statically placing them against those bosses in their seating and lying postures, but also load angle with respect to those vital points can be freely adjusted at their disposal.

11 Claims, 15 Drawing Sheets

F I G. 20
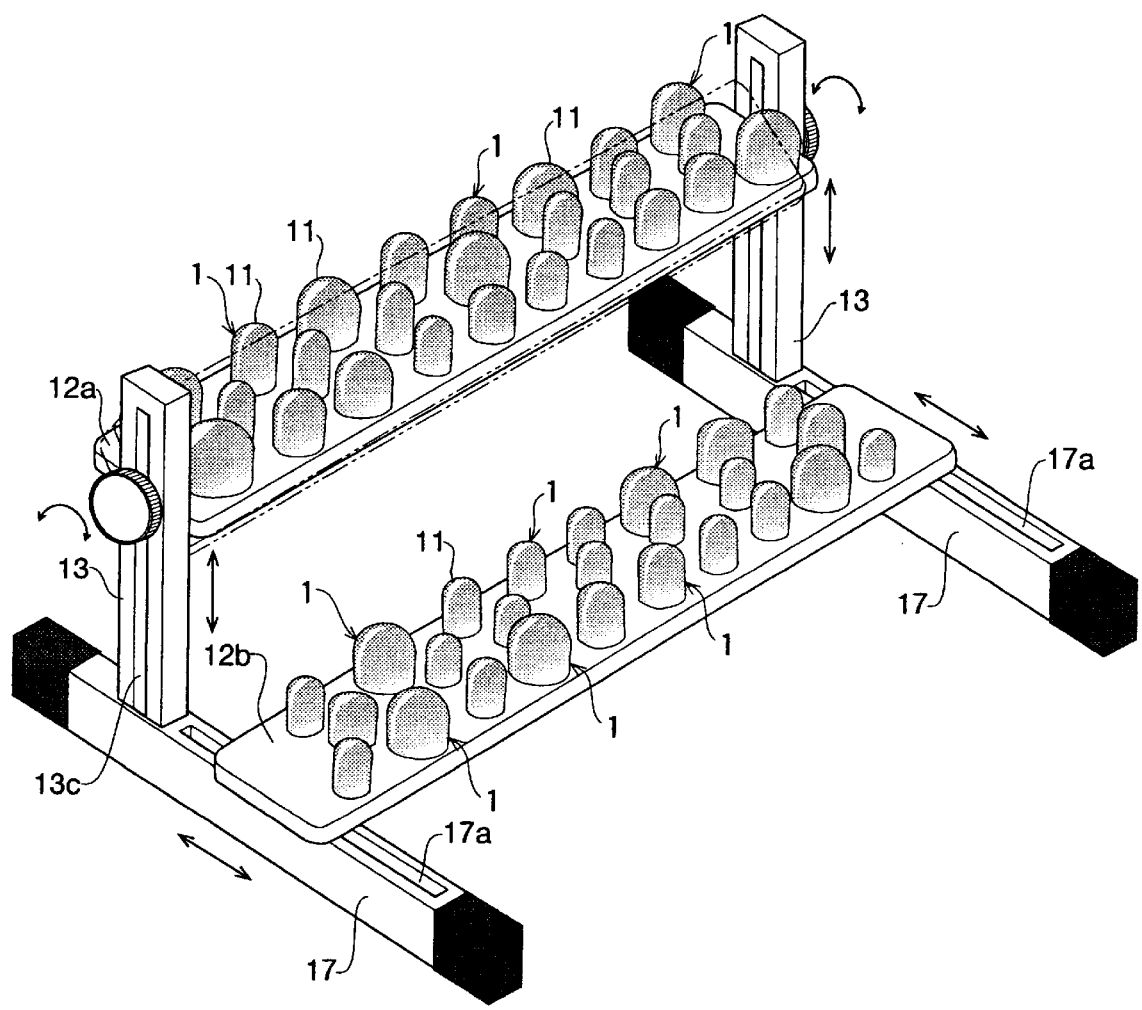

MASSAGING DEVICE FOR FEET AND LEGS

Applicant hereby claims the priority of Japanese Patent Application No. 9-34036, dated Feb. 18, 1997.

BACKGROUND OF THE INVENTION

The present invention relates to a massaging device for feet and legs, in more detail, it relates to a practical massaging device for feet and legs wherein vital points (or "tsubo" in Japanese) sporadically found in those body portions can be comfortably and adequately stimulated from most ideal angle with respect to those vital points by statically pressurizing them in one's seating and lying postures, so that the users can obtain satisfactory and favorable result of the treatment.

It is believed in an oriental medicine that there exist a number of the vital points relating to internal organs and cerebral nervous system and forming a part of "keiraku" in Japanese or a complicated network through which the vital energy essential to sustain our body flows on the soles of the feet and the calves of the legs generally considered as a mere human organ for walking. In old ages when the men lived in a primitive way, they walked on the rocky mountains and the fields full of stone and pebbles on barefoot so that their feet and legs were always subjected to continuous stimulation without realizing it, with the result that the primitive were invulnerable to such nervous disorder of internal organs and humor or endocrine and exocrine glands as we have at present.

However, as we have become more civilized, we have come to more often use a foot-covering with hard sole such as a pair of shoes and wooden footgear. Even though we now encourage ourselves to walk and jog every day, we can not obtain the same stimulation on our feet as in the primitive ages because the roads have become paved and levelled. In particular, as we now tend to neglect walking because we have accustomed to using transportation means such as cars and trains, the stimulation on the vital points of our feet and legs is not enough to prevent the disorder of nervous system as well as endocrine and exocrine glands, with the result that many of us suffer from dysautonomia, stiff shoulders and legs as well as loins pain or internal organ disease such as gastric and duodenal ulcer. This is the destiny of human beings who evolved from quadrupeds and began to walk wearing a foot-covering with hard sole on their feet so that they are chronically lacking in the stimulation on their feet and legs from their environment.

Under the circumstances, various types of massaging devices have been proposed to stimulate the vital points of the feet. The most popular device among them is a so-called "massaging device made of a spieces of a thick-stemmed bamboo wedged half in section". This device is used by placing it on the floor with its semi-circular surface facing upwards and is intended to stimulate the soles of the feet with said semi-circular surface when the users stand on the device barefoot and step on its surface repeatedly. Therefore, each time the users step on the semi-circular surface, the feet are pressurized against this surface so that they feel like being massaged on the feet by hand.

However, this prior device has been found inconvenient to use not only because all the vital points sporadically found on the feet can not be selectly and properly stimulated and the other portions of the feet soles besides those vital points are also pressurized as the feet are directly placed with respect to the semi-circular surface, a favorable effect can not be highly expected of this device considering that it gives hard pain to the feet supporting the whole weight of the user, but also because this device requires a considerable sense of balance, of course, though it does not need such a fine balance as required for walking on a thin rope as a ropedancer, it surely gave hard time to the elderly people, for instance.

Then, in order to solve the inconveninces of the aforesaid prior massaging device, "a massaging mat the surface of which the users step on" has been proposed as an improved device wherein a number of fingerlike elastic projections (B·B·) are mounted on the surface of an elastic rubber mat (Mt) as shown in FIG. 1. This improved device can more selectly pressurize the vital points of the feet and requires less sense of balance than the firstly mentioned prior art, but it gives effect also on the premise that the users stand on the mat and step on its surface. Therefore, if the projections (B·B··) are hardend too much, it gives hard pain to the users whereas if they are softened too much in order to abate the pain, they subside so easily that they can not properly stimulate those vital points.

The most incovenience common in both those prior arts, among others, is that the users tend to neglect using them according to the passage of time and even though the users are industrious enough to keep using them, they have to oblige themselves to keep making such an extraordinary stepping motion as mentioned above each time they like to use in the office so that they come to hesitate using them concurrently at work.

SUMMARY OF THE INVENTION

In view of the aforesaid inconveniences encountered in the prior arts, the present invention is to provide a convenient massaging device for feet and legs capable of using concurrently while the users are at desk in the office without any interruption.

Also, the present invention is to provide a practical massaging device for feet and legs capable of comfortably and adequately stimulating the vital points of those body portions from an appropriate angle with respect to those points not by pressurizing them with the whole weight of the user as in the prior arts, but by statically pressurizing them in his/her seating or lying posture.

Furthermore, the present invention is to provide a very convenient massaging device for feet and legs capable of effectively stimulating the vital points of those body portions by selecting load angle regarding those points that is appropriate for even the elderly people with less sense of balance or pain-prone users.

That is to say, to solve the aforesaid technical issues of the prior arts, the present invention is characterized in that it has adopted a massaging device for feet and legs wherein the vital points of those body portions can be comfortably and adequately stimulated by mounting those vital points on a number of spherically headed bosses lined in rows with a predetermined interval between adjacent bosses on platforms.

BRIEF DESCRIPTION OF THE DRAWINGS

FIG. 20 is a perspective view showing another modified embodiment of the present invention where the height of the upper platform can be adjusted by means of slits each provided on right-and-left columns while the position of the lower platform can be adjusted by means of slits each provided on right-and-left base bars.

DESCRIPTION OF THE PREFERRED EMBODIMENT

First Embodiment

Hereinafter, the best mode for carrying out the invention is described in reference to the accompanying drawings.

Figure 1:
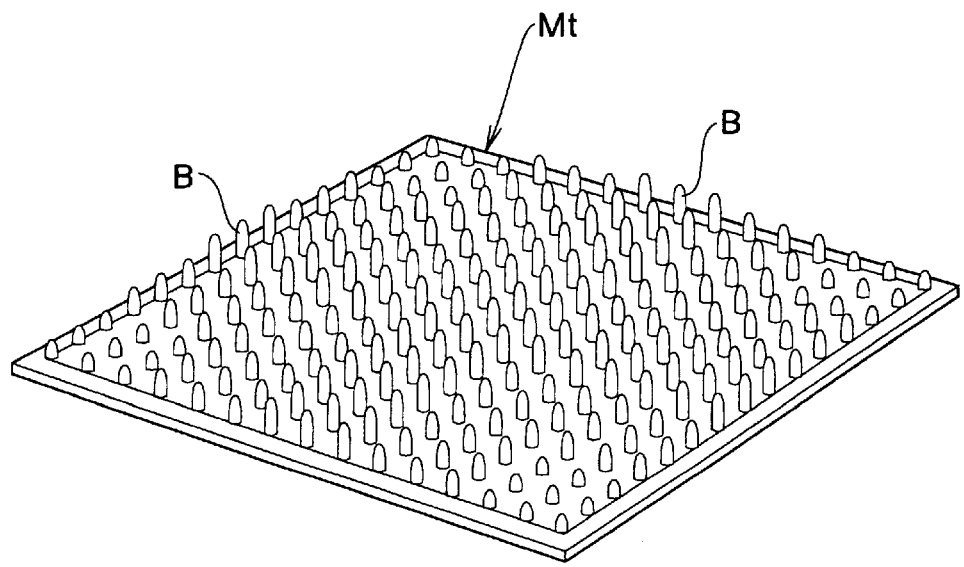
FIG. 1 is a perspective view of the prior art known as "a massaging mat the surface of which the users step on".
Figure 2:
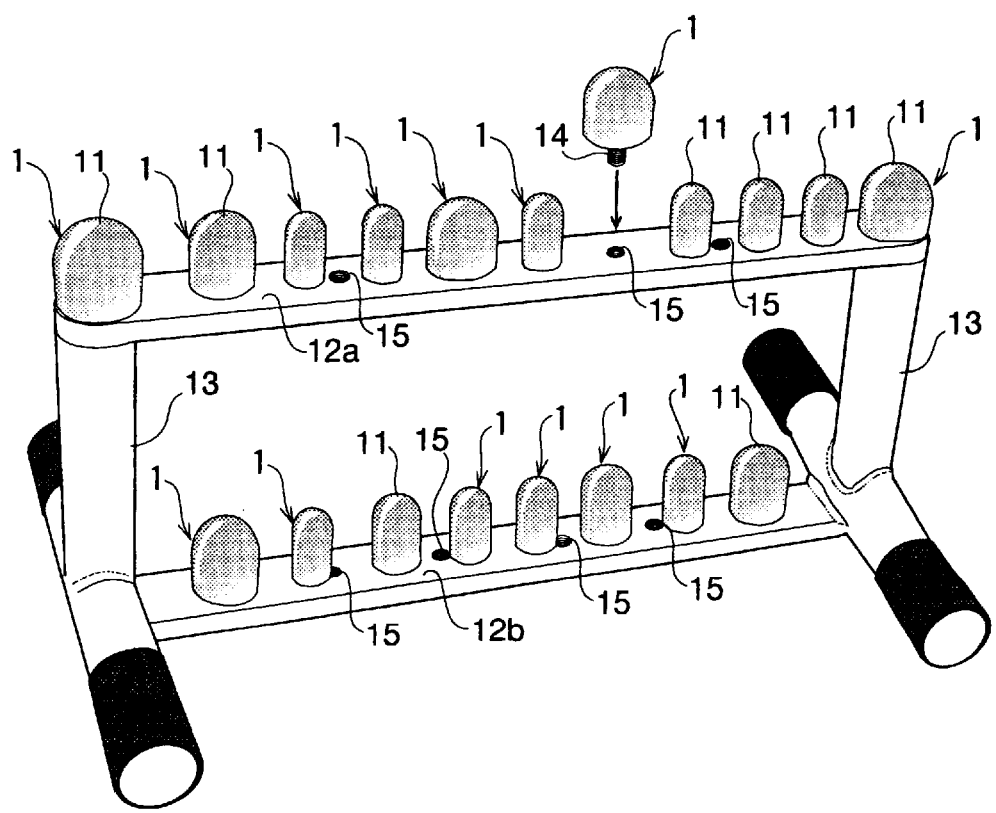
FIG. 2 is a perspective view of a massaging device for feet and legs described in the first embodiment of the present invention.

The first embodiment of the present invention is as shown in FIG. 2. Numeral (1·1···) in FIG. 2 indicates a boss to pressurize the vital points of feet and legs. In this embodiment, there are used four types of bosses with different diameter and the head portion (11) thereof is spherically shaped in each diameter.

Then, said bosses (1) are lined in one row with a subustantially equal interval spaced between adjacent bosses and removably mounted on the top surface of both an upper platform (12a) and a lower platform (12b) respectively suspended between right-and-left columns (13) and (13). The top surface of said upper platform (12a) is positioned about 15 cm above the floor level while the top surface of said lower platform (12b) is positioned about 3 cm above the floor level. And a spherically headed portion (11) of each boss (1) is positioned about 2.5 cm above the top surface level of said platforms (12a) and (12b) respectively.

Figure 3:
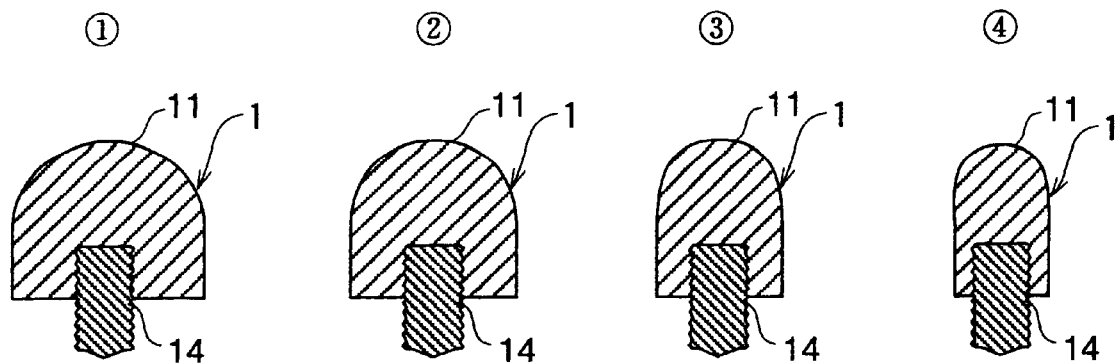
FIG. 3 at ① to ④ shows an elevational view in section of each boss used in the first embodiment of the present invention.

Then, in this embodiment, each boss (1) has uniformly 2.5 cm in height. The largest boss has 3 cm in diameter (refer to FIG. 3 at ①) and the one a little smaller than the largest one has 2.5 cm in diameter (refer to FIG. 3 at ②) while the smallest one has 1.5 cm in diameter(refer to FIG. 3 at ④) and the one a little larger than the smallest one has 2 cm in diameter (refer to FIG. 3 at ③). The boss (1) is made of soft iron and plated with nickel-chrome alloy on the surface while a screwed rod (14) is provided on the bottom portion. And boss installation portions (15·15···) (threaded bores as shown in the drawings) are provided on the top surface of the platforms (12a) and (12b) respectively so that the positioning of the boss (1) can be freely selected at the users' disposal. By installing the required number of bosses (1) into as many boss installation portions (15·15···) as the users think appropriate, it is possible to assemble a massaging device for feet and legs for pressurizing the very vital points of those body portions that the users really want to be stimulated.

Second Embodiment

Figure 4:
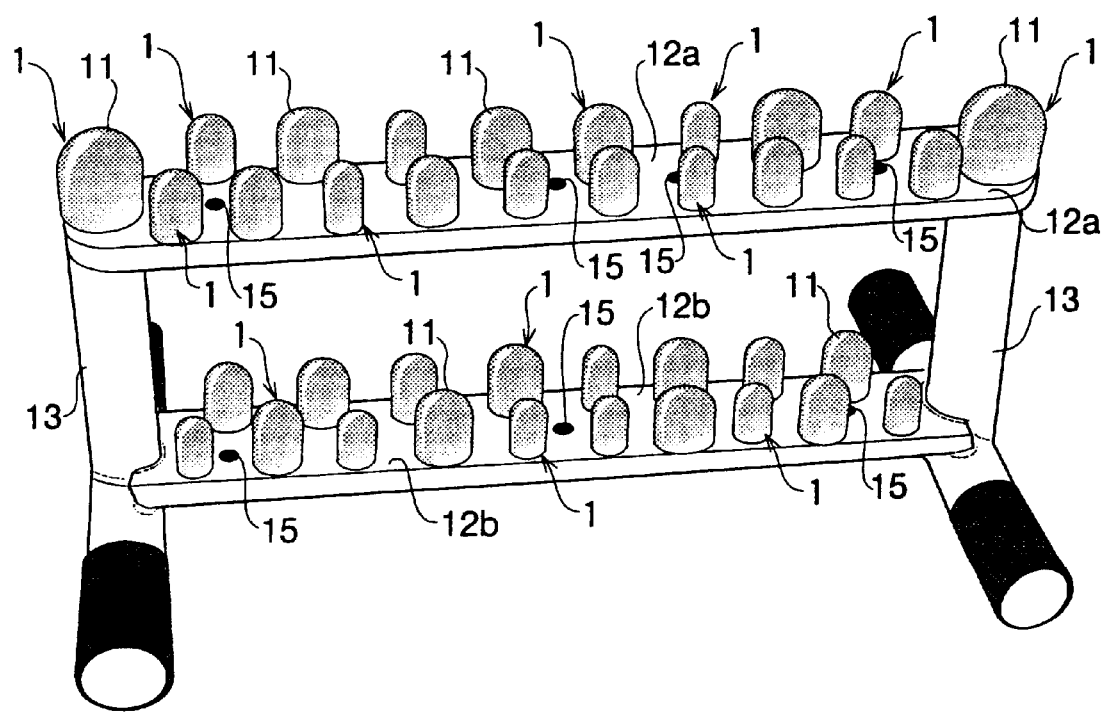
FIG. 4 is a perspective view of a massaging device for feet and legs described in the second embodiment of the present invention.

The second embodiment of the present invention is as shown in FIG. 4. The structural difference between the first embodiment and this one is in that the bosses(1·1···) are lined in two rows on the platforms (12a) and (12b) respectively while the functional difference therebetween is in that a permanent magnet (M) (samarium magnet equivallent to 1500 gauss) is incorporated into each boss (1).

Figure 5:
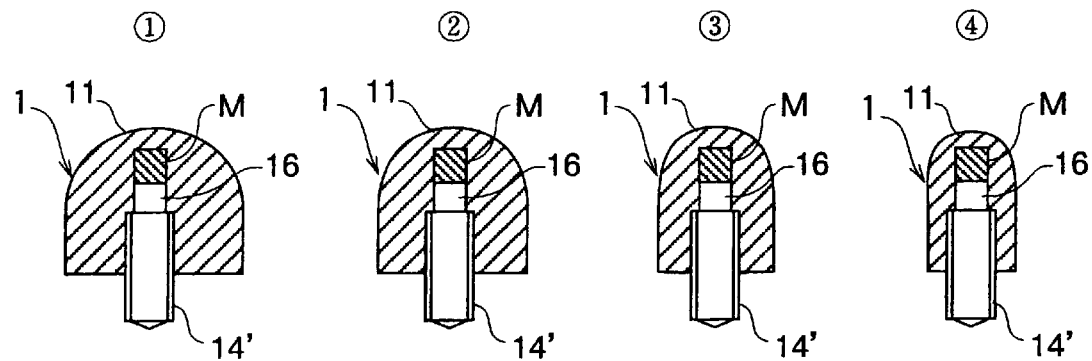
FIG. 5 at ① to ④ shows an elevational view in section of each boss used in the second embodiment of the present invention.

To give further comment on the aforesaid functional characteristics of the present embodiment, as shown in FIG. 5, a hole (16) is hollowed in each boss (1) extending from the center of the bottom portion to the upper portion thereof and a screwed rod (14') is screwed in internal threads notched on the lower part of said hole (16) while said permanent magnet (M) is incorporated into an uppermost cavity portion of the hole (16).

In this way, because a massaging device of the present embodiment stimulates the vital points of feet and legs synergistically or not only by pressurizing those points with the bosses, but also by applying magnetism to those points, the users can obtain satisfactory and comfortable result of the treatment.

Third Embodiment

Figure 6:
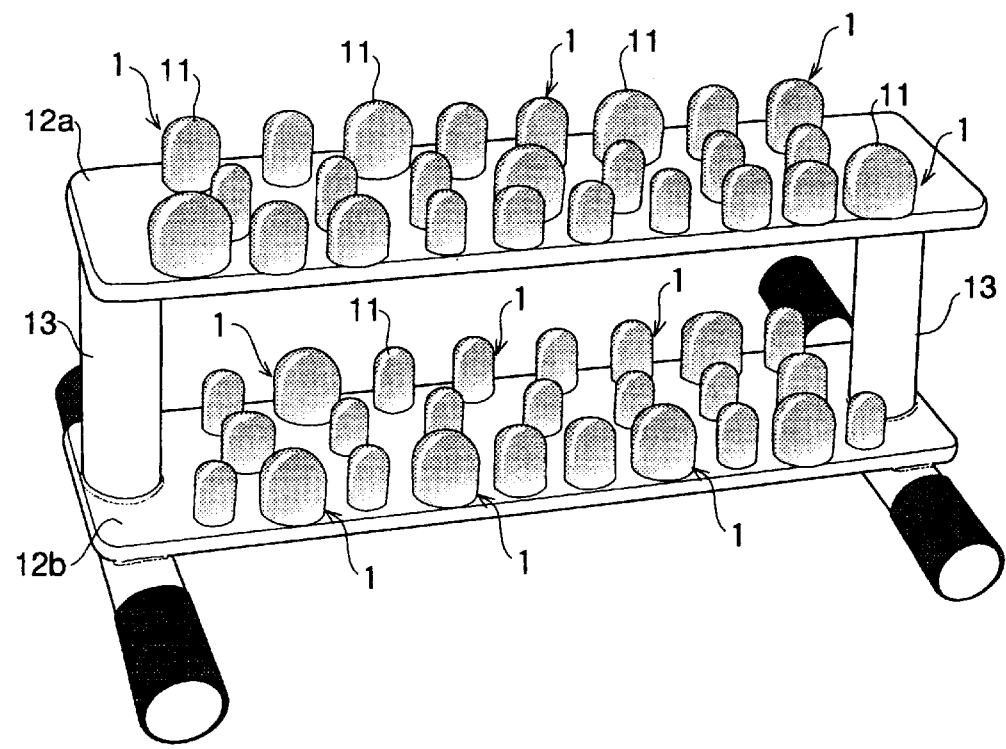
FIG. 6 is a perspective view of a massaging device for feet and legs described in the third embodiment of the present invention.

The third embodiment of the present invention is as shown in FIG. 6. The structural difference between the second embodiment and this one is in that the bosses (1·1···) are lined in three rows on the platforms (12a) and (12b) respectively and the functional difference therebetween is in that the contents of a so-called "portable warmer" or platinum powder adhered to rock wool (H) is incorporated into each boss (1) and the spherically headed portion (11) of the boss is heated to a required temperature by igniting the rock wool which has preliminarily absorbed volatile oil.

Figure 7:
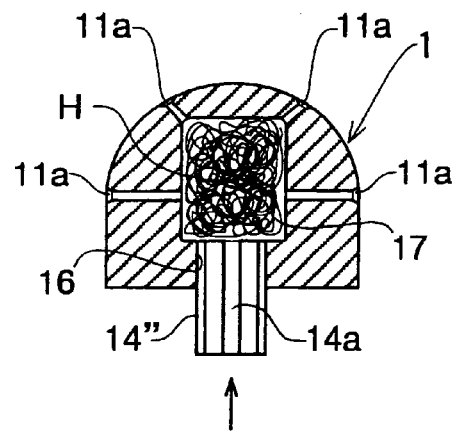
FIG. 7 is an elevational view in section of the boss used in the third embodiment.

To give further comment on the aforesaid functional characteristics of the present embodiment, as shown in FIG. 7, a hole (16) is hollowed in each boss (1) extending from the center of the bottom portion to the upper portion thereof and a screwed rod (14") is screwed in internal threads notched on the lower part of said hole (16) while the platinum powder adhered to the rock wool (H) is incorporated into an uppermost cavity portion of the hole (16). This platinum powder can be ignited by pouring volatile oil on said rock wool after having unscrewed said screwed rod (14") and be heated to the required temperature by taking in oxygen from an intake hole (14a) of the rod(14") while by exhausting carbon dioxide from an outlet (11a) provided on the spherically headed portion (11) of the boss.

In this way, because a massaging device of the present embodiment stimulates the vital points of feet and legs synergistically or not only by pressurizing those points with the bosses, but also by applying heat to those points, the users can obtain satisfactory and comfortable result of the treatment.

Fourth Embodiment

Figure 8:
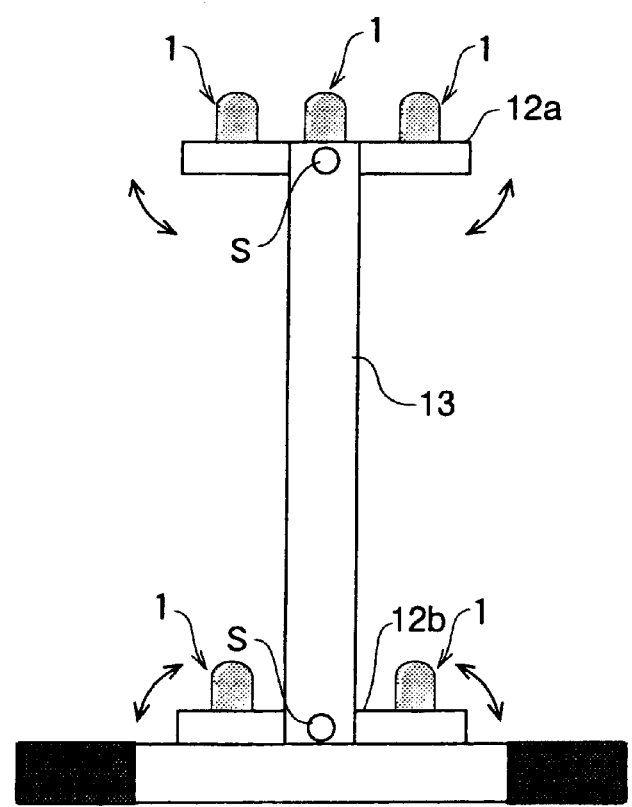
FIG. 8 is a side view of a massaging device described in the fourth embodiment of the present invention wherein the upper platform can be tilted to and fro.

The fourth embodiment of the present invention is shown in FIG. 8. This embodiment is the same as the third one in that the bosses(1·1···) are lined in three rows on the platforms (12a) and (12b) respectively. The difference therebetween is in that the upper platform (12a) suspended between right-and-left columns (13) and (13) can be tilted to and fro taking a pivotal axis (S) as a center.

Figure 9:
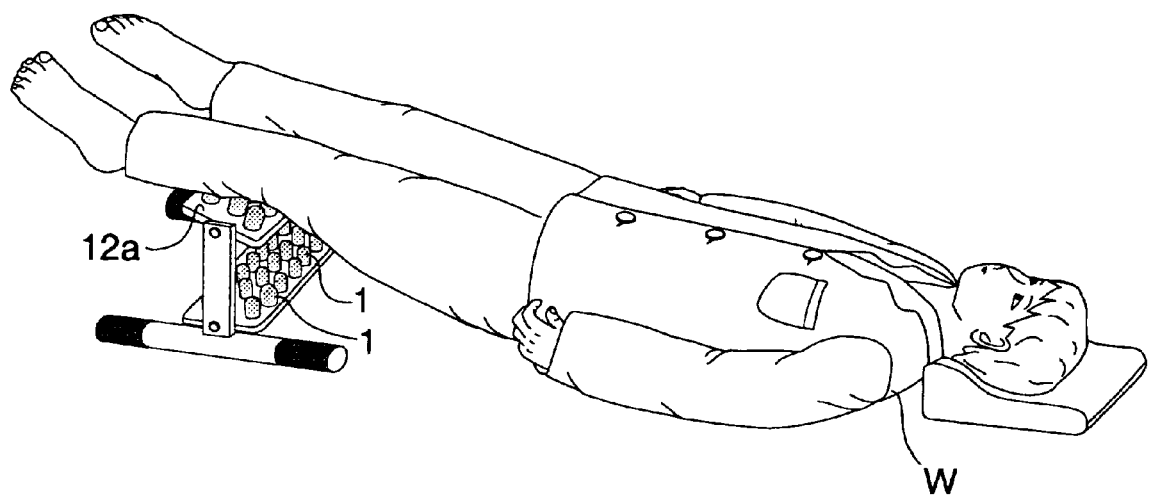
FIG. 9 is an explanatory view showing the state where a massaging device of the fourth embodiment is used.

In this way, with a massaging device of the present embodiment, as shown in FIG. 9, because the angle of the upper platform (12a) can be justly adjusted according to the postures of the users and the angle of their feet, it is possible to abut the bosses (1) on the vital points of the soles of the feet and the calves at an optimum angle so that the users can obtain satisfactory and favorable result of the treatment.

Fifth Embodiment

Figure 10:
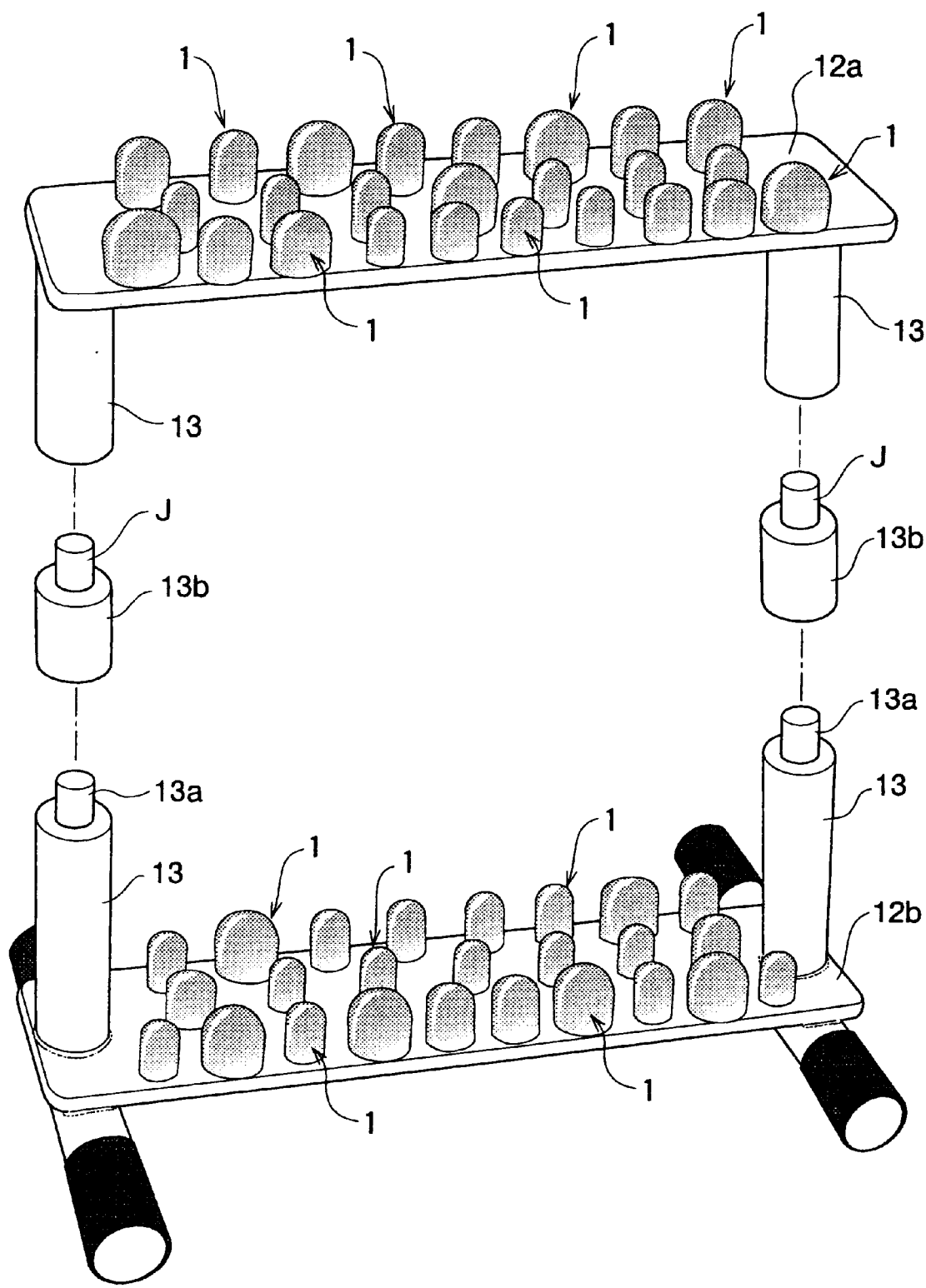
FIG. 10 is an exploded view of a massaging device of the fifth embodiment.

The fifth embodiment of the present invention is shown in FIG. 10. This embodiment is the same as the third embodiment in that the bosses (1·1···) are lined in three rows on the platforms (12a) and (12b) respectively. The characteristic feature of this embodiment is in that right-and-left columns (13) and (13) are each structured in a separable and add-on manner. That is to say, since a dowel (13a) provided on the upper end of the lower half portion of the column (13) is removably fitted into a cavity portion provided on the lower end of the upper half portion of the column (13), when the users want to raise the level of the upper platform (12a), the height of the column (13) can be adjusted by interposing a spacer (13b) between the lower half portion of the column (13) and the upper half portion thereof. More concretely speaking, the lower end of the spacer (13b) is hollow so as to receive said dowel (13a) while the upper end of the spacer (13b) is provided with a joggle (J) so as to be fitted into the cavity portion of the upper half portion of the column (13).

According to the fifth embodiment of the present invention, as the height level of the upper platform (12a) can be adjusted at the users' disposal, the users can position the height of the spherically headed portions of the bosses (1) so that they can obtain most comfortable and favorable stimulation on the vital points of their feet and legs.

(HOW TO USE)

The following is described to show how to use a massaging device of the present invention, supposing that it is used while the users are at desk in the office.

Figure 11:
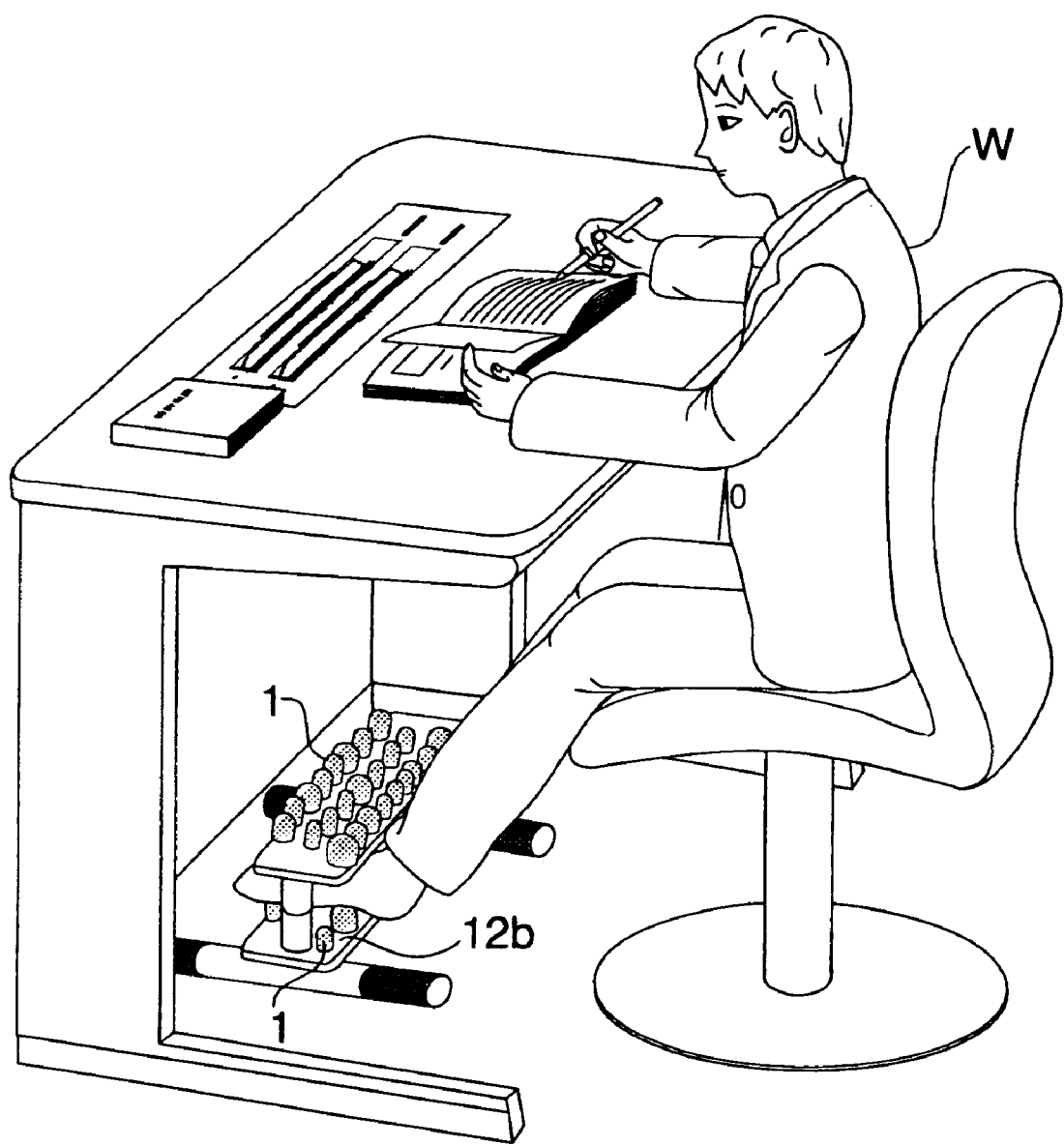
FIG. 11 is an explanatory view showing the state where the massaging device of the third embodiment is used (showing where the feet are mounted on the bosses lined in the lower platform.).
Figure 12:
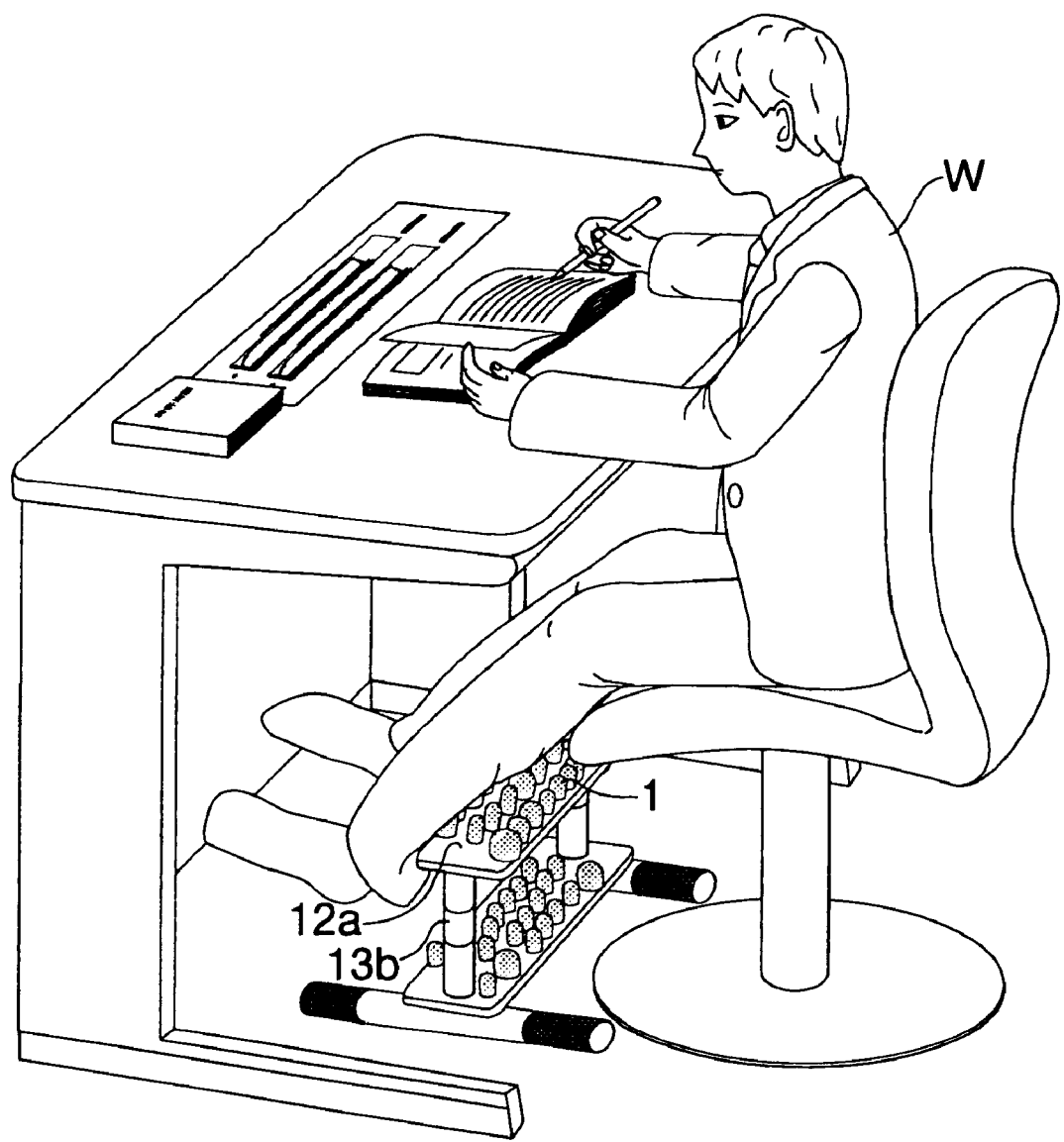
FIG. 12 is an explanatory view showing the state where the massaging device of the third embodiment is used (showing where the calves are mounted on the bosses lined in the upper platform.).

FIGS. 11 and 12 show the state where the vital points of the feet are stimulated with a massaging device of the third embodiment of the present invention.

In reference to FIG. 11, while a user (W) is at desk in the office, he mounts his feet on the bosses (1·1···) of the lower platform (12b) so as to stimulate the vital points thereof by statically placing them against those bosses in his seating posture. Even in such a posture as this, not only because the user can unconsciously stimulate the vital points of his feet, there is no case where it interrupts his work at all, but also because his feet are positioned about 6.0 cm above the floor level, the weight of his feet and legs is sufficiently carried on the bosses (1·1···) to justly stimulate those vital points.

Then, FIG. 12 shows the state where the user (W) at desk in the office mounts his calves on the bosses(1·1···) of the upper platform (12a). In this case too, the user (W) can continue his work without interruption at all, in the meanwhile, since the height level of the spherically headed portions (11) of the bosses (1·1···) is arranged about 17.5 cm above the floor level, he can obtain most adequate stimulation on the vital points of his calves so as to get rid of the fatigue on his feet and legs once and for all.

It is needless to say that the massaging device for feet and legs embodied in the present invention can be also applied to the users' lying posture. In this case, all the users have to do is to lie on their back and mount their calves on the bosses(1·1···) of the upper platform (12a) as shown in FIG. 9. In this way, the stagnated blood around the feet and legs immediately flows back to the heart, in the meanwhile, a vital point called "syouzan" positioned slightly below the central region of the calves is effectively stimulated.

The concrete embodiments of the present invention have been substantially described up to here, but it should be understood that the technical scope of the present invention is not limited to the aforesaid embodiments, but can be modified in various manners within the scope of the accompanying patent claims.

For instance, in the aforesaid third embodiment, the boss (1) made of soft iron and plated with nickel-chrome alloy is exemplified, but it is no problem either to use a boss of synthetic resin processed by injection molding or casting, sintered ceramic, cast metal such as die cast aluminum, powder metallurgical product or of wooden material such as teakwood or an artificial panel board and particle board. As to the aforesaid boss made of synthetic resin, it is also possible to adopt one with its surface colored in gold or silver by means of such a well-known surface treatment method as ion plating or vacuum deposition.

On the other hand, although platinum powder adhered to rock wool contained in a portable warmer is adopted as a heating element to be incorporated into the boss (1) in the third embodiment, it is also possible to cauterize the vital points of the feet and legs by incorporating a combustible containing moxa substance, e.g., "moxibustion" manufactured by "Sennenkyu Co.,Ltd." into the boss (1). Likewise, such modified embodiment also belongs to the technical scope of the present invention as conducting to the boss (1) the thermal energy of an electrical ribbon heater (not shown in the drawings) installed under the upper and lower platforms (12a) and (12b) respectively by means of a holding member such as magnet.

Further, instead of said heating element incorporated into the boss of the third embodiment of the present invention, it is also possible not only to restrain bad ordor of the sudoriferous feet by incorporating a deodorant such as active carbon and zeolite into the boss, but also to refresh or relax oneself by incorporating perfume or aromatics into the boss. It is needless to say that those modified embodiments also belong to the technical scope of the present invention.

Figure 13:
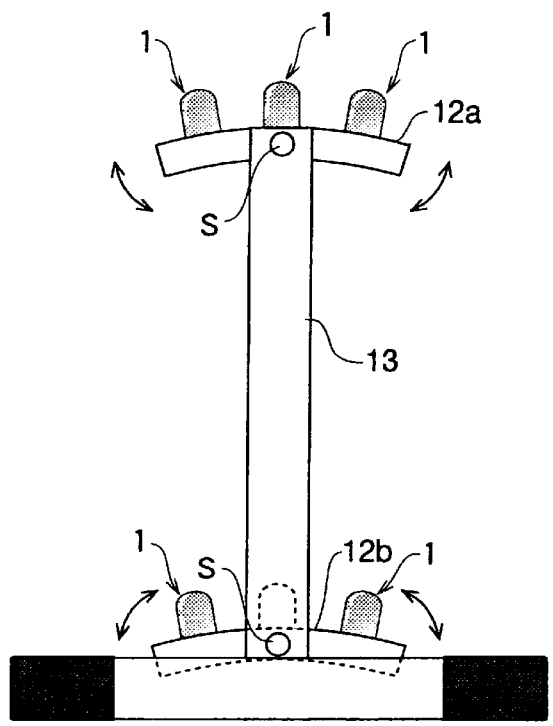
FIG. 13 is a side view showing a modified embodiment of the present invention where the platforms are archly structured in section.
Figure 14:
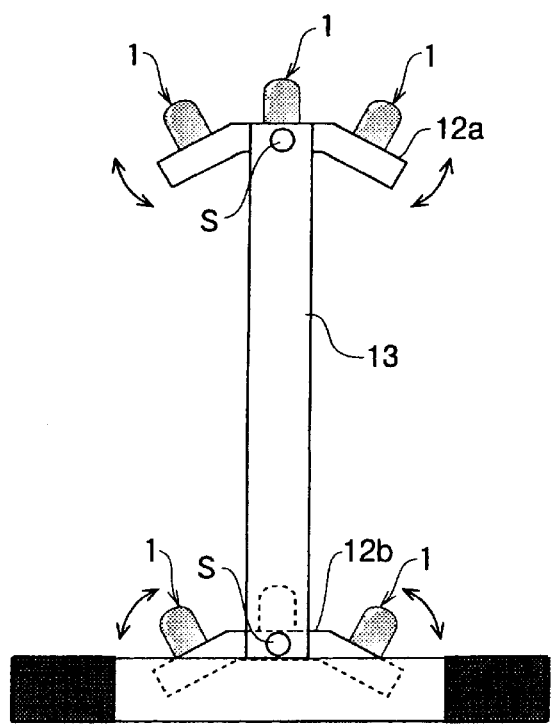
FIG. 14 is a side view of another modification of the present invention where the platforms are trapizoidally structured in section.

Moreover, it is also possible to make the upper and lower platforms (12a) and (12b) in the fourth embodiment of the present invention archly or trapizoidally shaped in section as shown in FIG. 13 and 14. Because load angle with respect to the vital points of the feet and legs becomes optimum just with those shapes, it does not necessarily arrange the platforms so that they can be tilted to and fro. The FIGS. 13 and 14 show those platforms (12a) and (12b) archly or trapizoidally structured in section capable of being tilted to and fro, but they are disclosed in order to realize further optimum load angle with respect to the vital points. It rather should be understood that the present invention does not matter whether the platforms having such various shapes as mentioned above can be tilted to and fro.

Figure 15:
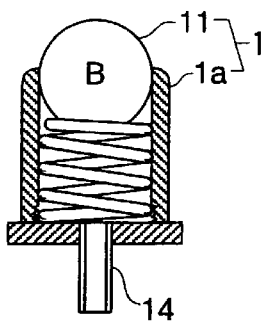
FIG. 15 is an elevational view in section of a boss the spherically headed portion of which consists of a rotatable ball showing another modified embodiment of the present invention.

Then, in any of the aforesaid embodiments, it is disclosed that the spherically headed portion of the boss (1) is in integral structure with the body portion thereof. However, it is also possible to adopt another boss (1) wherein the spherically headed portion thereof is arranged by rotatably incorporating a ball (B) into the upper part of a body portion (1a) as shown in FIG. 15 in order to realize much smoother contact with the feet and legs of the users. This modified embodiment belongs to the technical scope of the present invention.

Figure 16:
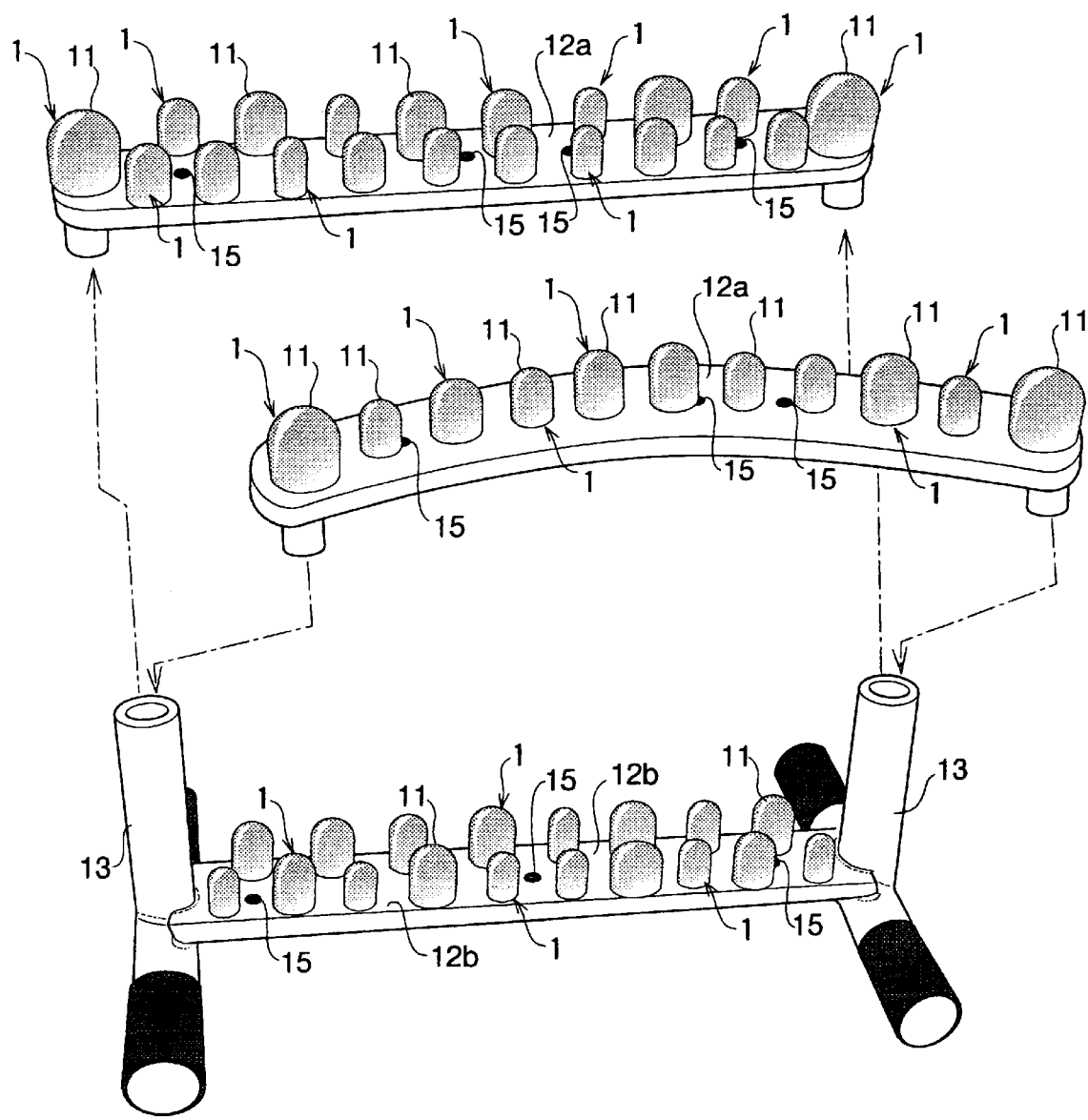
FIG. 16 is a perspective view showing another modified embodiment of the present invention where a removably mounted platform is being pulled out of both columns and is being replaced with a curved platform.

Likewise, it is also possible to arrange the upper and lower platforms (12a) and (12b) so that they can be removed from the columns (13) as shown in FIG. 16. In this case, by keeping various types of platforms in stock, the users can exchange a plane platform with another (e.g., a curved type, an archly or trapizoidally structured type in section, etc.) so that it becomes more convenient to select more appropriate platform to satisfy their needs. In addition to this, the users can carry the massaging device embodied in the present invention with them wherever they go by dismounting it so that it facilitates them to use it on travel or on board. Such modified embodiments also belong to the technical scope of the present invention.

Figure 17:
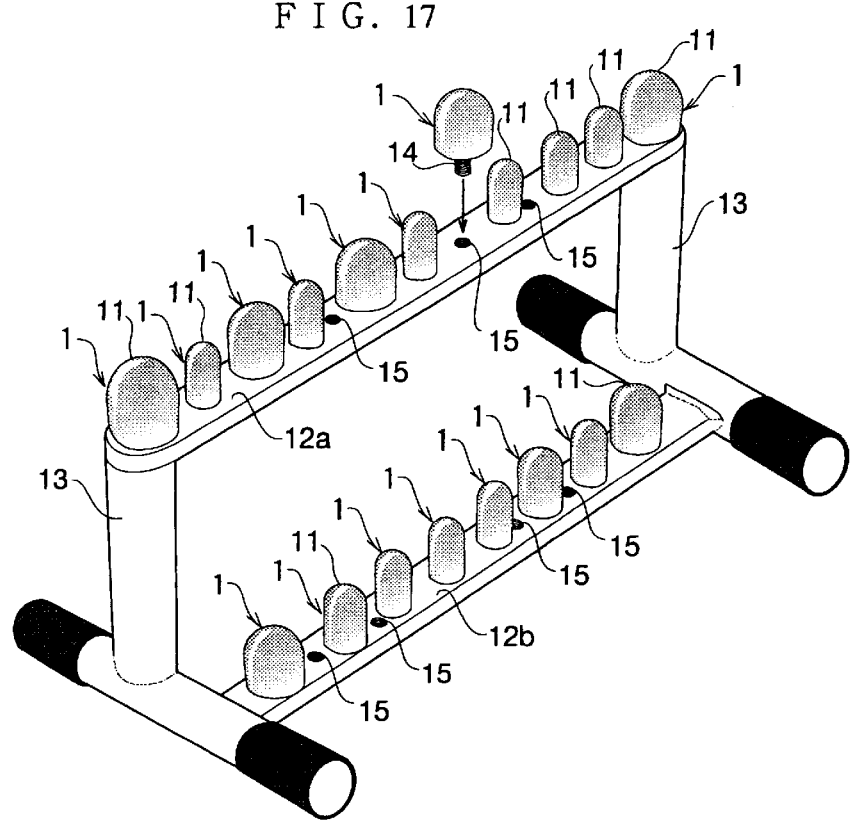
FIGS. 17 to 19 are perspective views showing another modified embodiment of the present invention where the upper platform is arranged with regard to the lower platform in stepwise manner.
Figure 18:
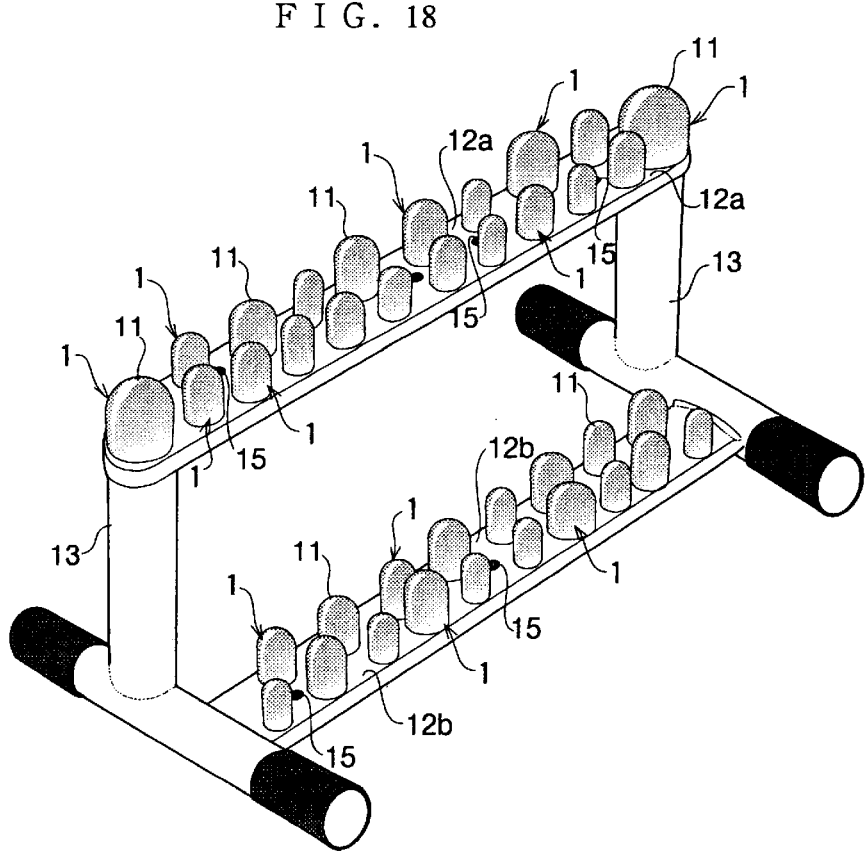
Figure 19:
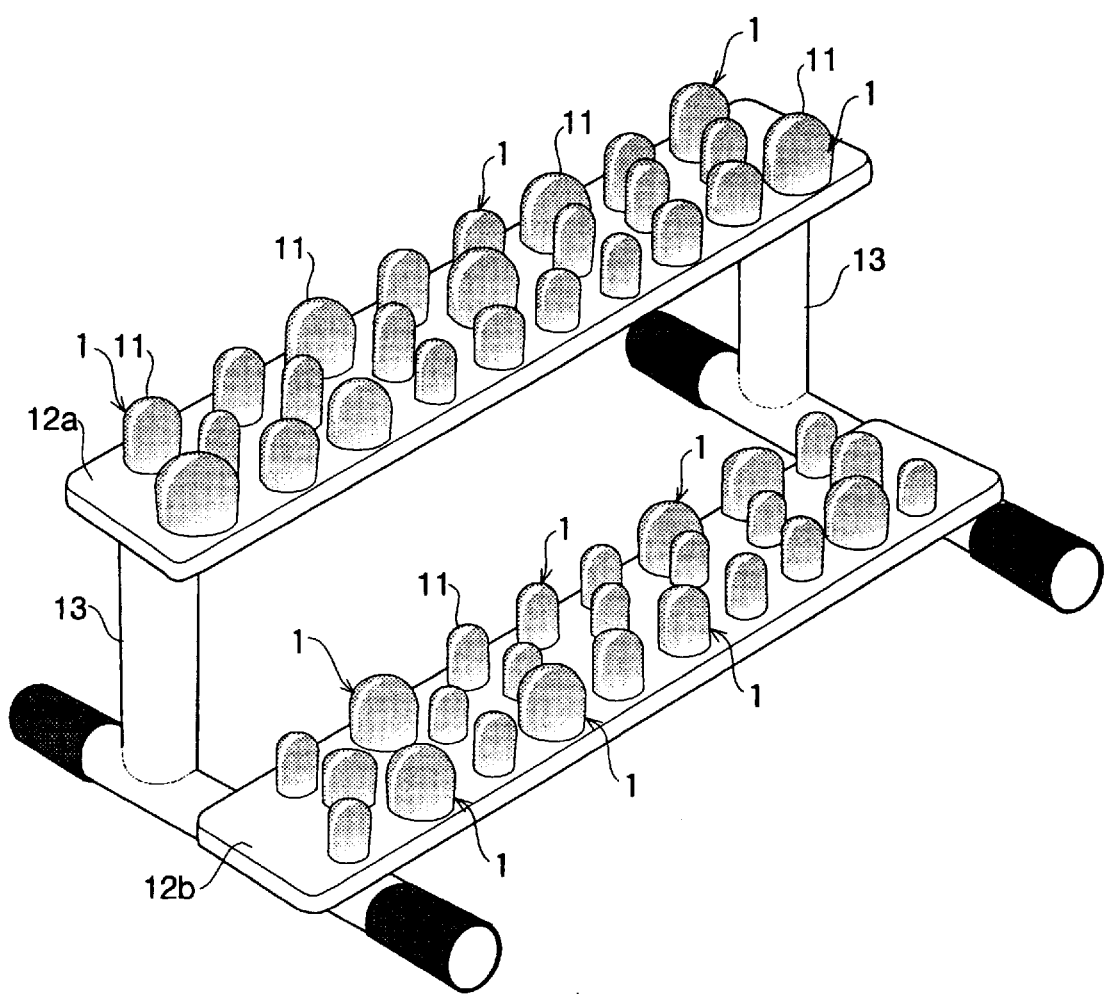

Then, in any one of the first to the fifth embodiments of the present invention, the upper and lower platforms (12a) and (12b) are arranged in such a manner that the former is positioned directly above the latter in the drawings, but it is an obvious modified embodiment of the present invention to arrange the upper platform (12a) and lower platform (12b) in stepwise manner as shown in FIGS. 17 and 18.

Then, in the fifth embodiment of the present invention, it is disclosed that the height of the upper platform (12a) is raised by interposing a spacer (13b) between the upper and lower half portion of the columns (13). However, instead of said spacer, it is also possible either to adjust the height of the upper and lower platforms (12a) and (12b) respectively without taking a stepwise adjustment by adopting a well-known adjusting bolt mechanism or, as shown in FIG. 20, to adjust the height of the upper platform (12a) by means of a knob and slit (13c) provided on right-and-left columns (13) and (13) respectively which support the platform (12a) while to adjust the back-and-forth position of the lower platform (12b) by means of a knob and slit (17a) provided on base bars (17) and (17) respectively. Those modified embodiments also belong to the technical scope of the present invention.

Figure 21:
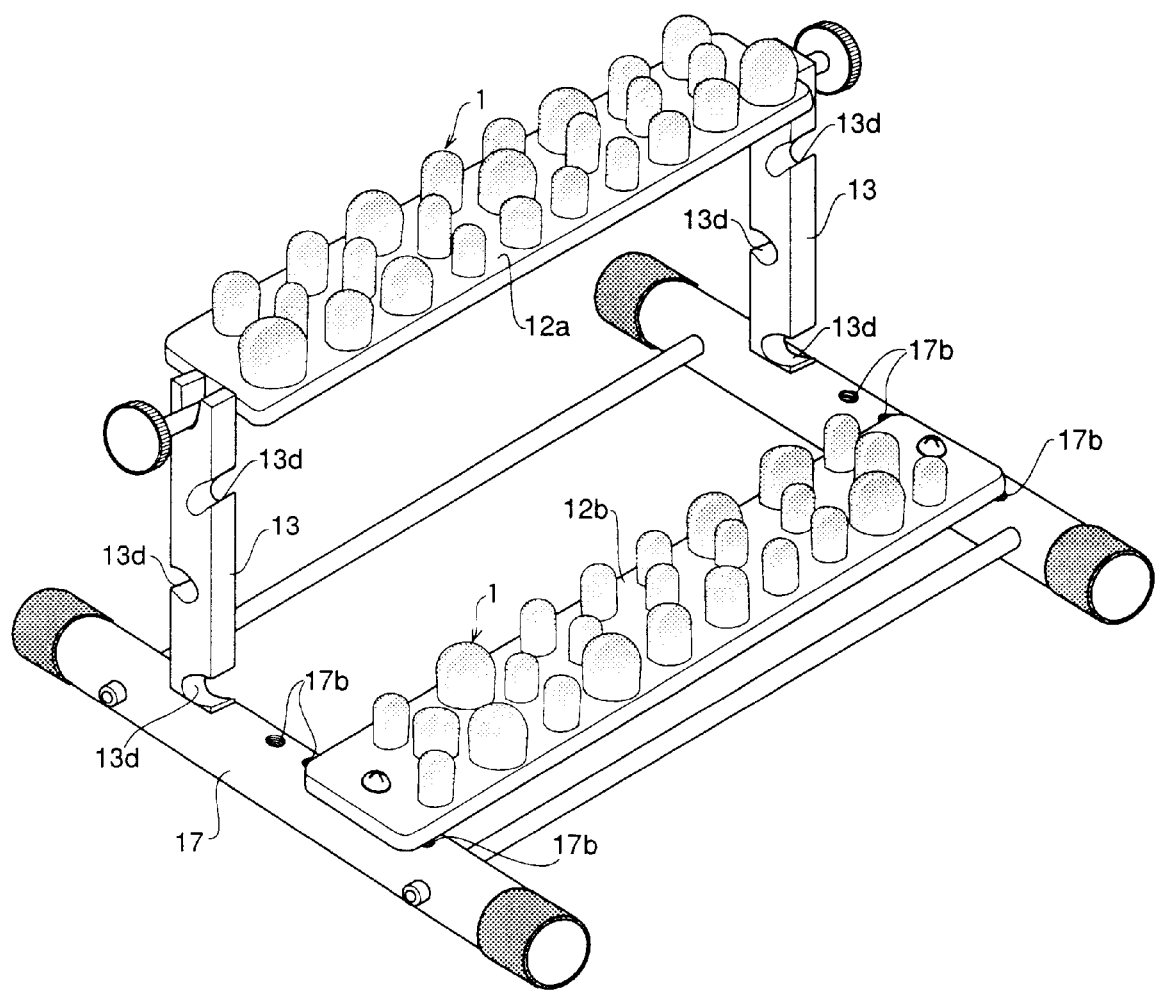
FIG. 21 is a perspective view showing another embodiment where the height of the upper platform can be adjusted by means of brackets each provided on both columns while the position of the lower platform can be adjusted by means of threaded holes provided on the base bars.
Figure 22:
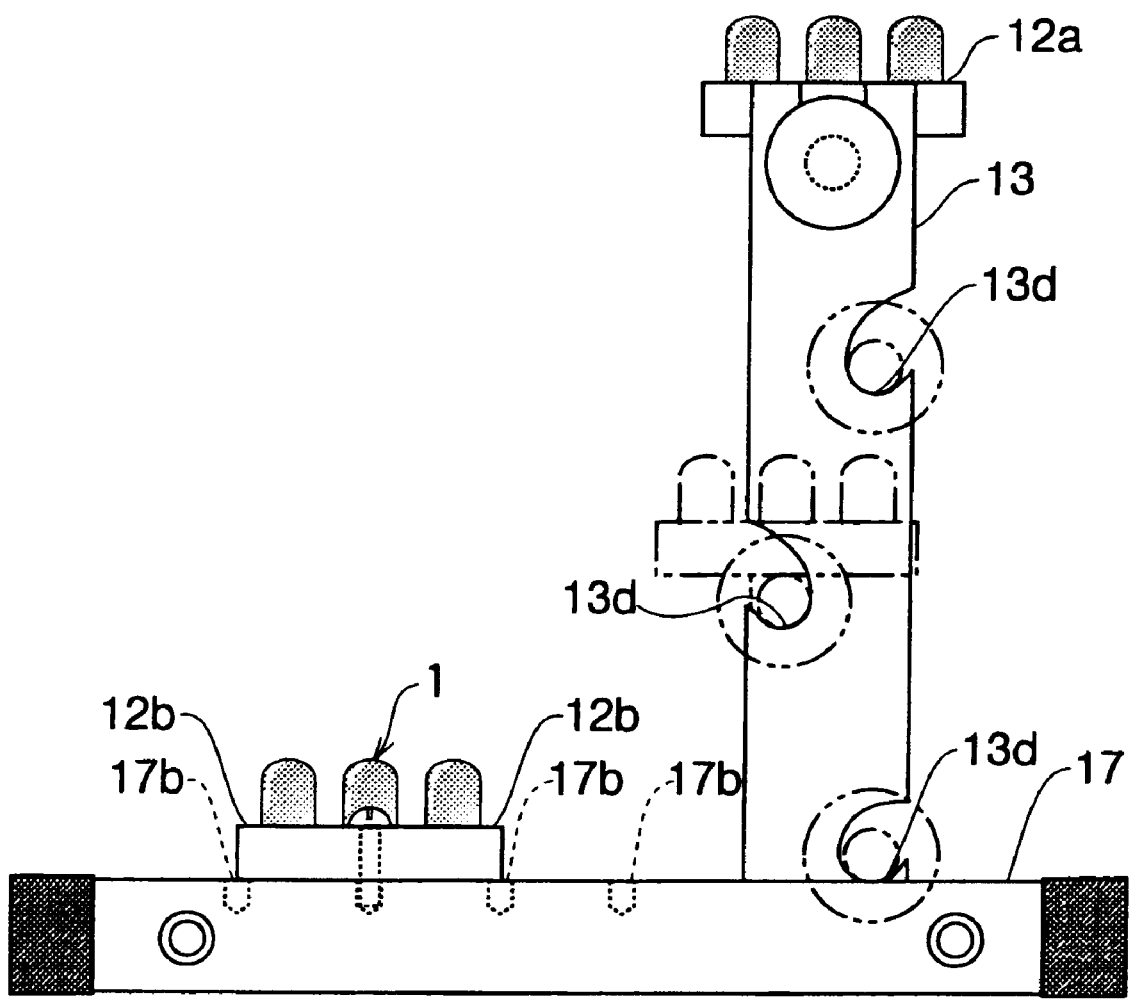
FIG. 22 is a side view of the massaging device shown in FIG. 21.

Likewise, another modified embodiment of the present invention is shown in FIG. 21, where the height of the upper platform (12a) can be adjusted by means of brackets (13d·13d··) provided on the side surface of right-and-left columns (13) and (13) respectively to support both end portions of the upper platfrom (12a) while the position of the lower platform (12b) can be adjusted back and forth by means of threaded holes (17b··) provided on the upper surface of the base bars (17) with a certain interval placed therebetween. This modified embodiment also belongs to the technical scope of the present invention.

Moreover, in the aforesaid embodiments of the present invention, the bosses(1·1··) are screwed in the upper and lower platforms (12a) and (12b) by way of any one of the screwed rods (14), (14')and (14"), but they also can be fixed just by partly fitting their body portions into holes bored in the platforms or by mounting them via bayonet caps. Further, it is also possible to install those bosses slidably broadwise or to attach them to the platforms (12a) and (12b) by taking advantage of permanent magnet (M) incorporated into the bosses as described in the second embodiment, of course, provided that those platforms are also made of magnetic. Such modified embodiments also belong to the technical scope of the present invention.

As having been described up to here in the aforesaid embodiments, with the massaging device for feet and legs embodied in the present invention, the users can obtain comfortable and satisfactory result of the treatment just by placing it below the desk or in front of the bench and then mounting their feet and calves on the bosses of the platforms without requiring either an exclusive exercise space or extraordinary motion and strong motivation on the users's part so that they can casually stimulate the vital points of their feet and legs concurrently while they are at desk in the office. Therefore, the massaging device embodied in the present invention is so convenient to use and handy to carry that the industrial applicability thereof is very high.

Further, with the massaging device embodied in the present invention, because it is possible to adequately and comfortably stimulate the vital points of the feet and calves as well as a vital point called "sanri" positioned on the outer lateral surface with respect to the shank from most ideal angle regarding those vital points not by pressurizing them with the body's weight, but by statically placing them against the bosses either in one's seating posture on the chair or the bench or in one's lying postures; on one's back, on one's face or on one's side, even the elderly people with less sense of balance can use it without trouble so that its practicability is very high.

Furthermore, with the massaging device embodied in the present invention, since load angle with respect to the vital points of the feet and legs can be freely adjusted by the users themselves, even pain-prone or obese users who could not have been obtained appropriate stimulation on the feet and legs with the prior massaging devices for the feet and legs can attain such stimulation as they feel appropriate so that it completely satisfies their needs.

According to the massaging device for feet and legs embodied in the present invention, such an excellent effect and operation as mentioned above can be achieved with a simple, but durable structure and in a cost-saving manner, which can not be expected of the prior arts such as "a massaging device made of a spieces of a thick-stemmed bamboo wedged half in section" or "a massaging mat the surface of which the users step on", so that its industrial applicability is very high.

What is claimed is:

1. A massaging device for feet and legs comprising:

a number of bosses each having a spherically headed portion which are lined in rows on platforms wherein said platforms are vertically spaced and aligned with an interval between adjacent bosses, wherein either feet or legs are laid on said platforms in a user's seating or lying posture in such a manner that a number of vital points found on those body portions abut on said bosses, wherein, said feet or legs are statically pressurized against the headed portions of said bosses to stimulate the vital points, wherein said platforms are removably and exchangeably structured, and wherein said platforms are vertically spaced from each other so that insteps of a user's feet do not abut an upper platform when the user's feet are placed on a lower platform boss.

2. A massaging device as claimed in claim 1, wherein there are platforms at least in two vertical stages each provided with said bosses on a platform top.

3. A massaging device as claimed in claim 1, wherein the bosses arranged on the top surface of the platforms are lined in plural rows.

4. A massaging device as claimed in claim 1, wherein a ball is rotatably incorporated into an upper part of the boss, thereby, forming a spherically headed portion thereof.

5. A massaging device as claimed in claim 1, wherein the bosses each contain a magnetic element, thereby, stimulating those vital points abutted on the bosses with magnetism in addition to physically pressurizing them with the bosses.

6. A massaging device as claimed in claim 1, wherein the bosses each contain a heating element, thereby, stimulating those vital points abutted on the bosses with heat in addition to physically pressurizing them with the bosses.

7. A massaging device for feet and legs comprising:

a number of bosses each having a spherically headed portion which are lined in rows on platforms wherein said platforms are vertically spaced and aligned with an interval between adjacent bosses, wherein either feet or legs are laid on said platforms in a user's seating or lying posture in such a manner that a number of vital points found on those body portions abut on said bosses, wherein, said feet or legs are statically pressurized against the headed portions of said bosses to stimulate the vital points, wherein the height of each platform having the bosses on the top surface is adjustable, and wherein said platforms are vertically spaced from each other so that insteps of a user's feet do not abut an upper platform when the user's feet are placed on a lower platform boss.

8. A massaging device as claimed in claim 7, wherein the bosses arranged on the top surface of the platforms are lined in plural rows.

9. A massaging device as claimed in claim 7, wherein a ball is rotatably incorporated into an upper part of the boss, thereby forming a spherically headed portion thereof.

10. A massaging device as claimed in claim 7, wherein the bosses each contain a magnetic element, thereby, stimulating those vital points abutted on the bosses with magnetism in addition to physically pressurizing them with the bosses.

11. A massaging device, as claimed in claim 7, wherein the bosses each contain a heating element, thereby, stimulating those vital points abutted on the bosses with heat in addition to physically pressurizing them with the bosses.

* * * * *